US00PP29523P2

(12) United States Plant Patent
Beekenkamp

(10) Patent No.: US PP29,523 P2
(45) Date of Patent: Jul. 17, 2018

(54) ***DAHLIA* PLANT NAMED 'BKDAMRD'**

(50) Latin Name: *Dahlia hybrida*
Varietal Denomination: BKDAMRD

(71) Applicant: Annie Cornelia Beekenkamp, Maasdijk (NL)

(72) Inventor: Annie Cornelia Beekenkamp, Maasdijk (NL)

(73) Assignee: Beekenkamp Plants B.V., Maasdijk (NL)

( * ) Notice: Subject to any disclaimer, the term of this patent is extended or adjusted under 35 U.S.C. 154(b) by 0 days.

(21) Appl. No.: 15/731,109

(22) Filed: Apr. 19, 2017

(51) Int. Cl.
*A01H 5/02* (2018.01)

(52) U.S. Cl.
USPC ..... Plt./321

(58) Field of Classification Search
USPC ..... Plt./321
See application file for complete search history.

(56) References Cited

PUBLICATIONS

PLUTO Plant Variety Database Feb. 24, 2018. p. 1.*

* cited by examiner

*Primary Examiner* — Annette H Para
(74) *Attorney, Agent, or Firm* — C. A. Whealy

(57) ABSTRACT

A new and distinct cultivar of *Dahlia* plant named 'BKDAMRD', characterized by its broadly upright and sturdy plant habit; freely basal branching habit; dense and bushy growth habit; dark green-colored leaves; and large semi-double inflorescences with bright red-colored ray florets.

2 Drawing Sheets

Botanical designation: *Dahlia hybrida.*
Cultivar denomination: 'BKDAMRD'.

BACKGROUND OF THE INVENTION

The present invention relates to a new and distinct cultivar of *Dahlia* plant, botanically known as *Dahlia hybrida* and hereinafter referred to by the name 'BKDAMRD'.

The new *Dahlia* plant is a product of a planned breeding program conducted by the Inventor in Maasdijk, The Netherlands. The objective of the breeding program is to create new sturdy container *Dahlia* plants that have a freely basal branching habit, and large inflorescences with attractive ray floret coloration.

The new *Dahlia* plant originated from an open-pollination in September, 2012 in Maasdijk, The Netherlands of a proprietary selection of *Dahlia hybrida* identified as code number 4002145, not patented, as the female, or seed, parent with an unknown selection of *Dahlia hybrida* as the male, or pollen, parent. The new *Dahlia* plant was discovered and selected by the Inventor as a single flowering plant from within the progeny of the stated open-pollination in a controlled greenhouse environment in Maasdijk, The Netherlands in October, 2013.

Asexual reproduction of the new *Dahlia* plant by terminal cuttings in a controlled greenhouse environment in Maasdijk, The Netherlands since February, 2014 has shown that the unique features of this new *Dahlia* plant are stable and reproduced true to type in successive generations.

SUMMARY OF THE INVENTION

Plants of the new *Dahlia* have not been observed under all possible combinations of environmental conditions and cultural conditions. The phenotype may vary somewhat with variations in environmental conditions such as temperature and light intensity, without, however, any variance in genotype.

The following traits have been repeatedly observed and are determined to be the unique characteristics of 'BKDAMRD'. These characteristics in combination distinguish 'BKDAMRD' as a new and distinct *Dahlia* plant:

1. Broadly upright and sturdy plant habit.
2. Freely basal branching habit; dense and bushy growth habit.
3. Dark green-colored leaves.
4. Large semi-double inflorescences with bright red-colored ray florets.

Plants of the new *Dahlia* differ primarily from plants of the female parent selection in the following characteristics:

1. Inflorescences of plants of the new *Dahlia* are larger than inflorescences of plants of the female parent selection.
2. Plants of the new *Dahlia* and the female parent selection differ in ray floret color as plants of the female parent selection have yellow-colored ray florets.

Plants of the new *Dahlia* can be compared to plants of *Dahlia variabilis* 'Carolina Burgundy', disclosed in U.S. Plant Pat. No. 13,635. In side-by-side comparisons, plants of the new *Dahlia* differ from plants of 'Carolina Burgundy' in the following characteristics:

1. Inflorescences of plants of the new *Dahlia* have more ray florets than inflorescences of plants of 'Carolina Burgundy'.
2. Plants of the new *Dahlia* and 'Carolina Burgundy' differ in ray floret color as plants of 'Carolina Burgundy' have dark red purple-colored ray florets.

BRIEF DESCRIPTION OF THE PHOTOGRAPHS

The accompanying photographs illustrate the overall appearance of the new *Dahlia* plant showing the colors as true as it is reasonably possible to obtain in colored reproductions of this type. Colors in the photographs may differ slightly from the color values cited in the detailed botanical description which accurately describe the colors of the new *Dahlia* plant.

The photograph on the first sheet comprises a side perspective view of a typical flowering plant of 'BKDAMRD' grown in a container.

The photograph on the second sheet is a close-up view of a typical inflorescence of 'BKDAMRD'.

DETAILED BOTANICAL DESCRIPTION

The aforementioned photographs and the following observations and measurements describe plants grown during the winter in 12-cm containers in a glass-covered greenhouse in Maasdijk, The Netherlands and under cultural practices typical of commercial *Dahlia* production. During the production of the plants, day and night temperatures ranged from 17° C. to 19° C. Plants were pinched one time and were nine weeks old when the photographs and description were taken. To induce inflorescence initiation and development, plants were grown under short nyctoperiod (long day) conditions. In the following description, color references are made to The Royal Horticultural Society Colour Chart, 2015 Edition, except where general terms of ordinary dictionary significance are used.

Botanical classification: *Dahlia hybrida* 'BKDAMRD'.

Parentage:

*Female, or seed, parent*.—Proprietary selection of *Dahlia hybrida* identified as code number 4002145, not patented.

*Male, or pollen, parent*.—Unknown selection of *Dahlia hybrida*, not patented.

Propagation:

*Type*.—By terminal cuttings.

*Time to initiate roots, summer*.—About 16 days at temperatures ranging from 18° C. to 21° C.

*Time to initiate roots, winter*.—About 19 days at temperatures ranging from 19° C. to 21° C.

*Time to produce a rooted young plant, summer*.—About 21 days at temperatures ranging from 18° C. to 21° C.

*Time to produce a rooted young plant, winter*.—About 23 days at temperatures ranging from 19° C. to 21° C.

*Root description*.—Medium in thickness, fibrous; typically creamy white to light brown in color, actual color of the roots is dependent on substrate composition, water quality, fertilizers, substrate temperature and physiological age of roots; tuber development has not been observed on plants of the new *Dahlia*.

*Rooting habit*.—Moderately freely branching; medium density.

Plant description:

*Plant and growth habit*.—Broadly upright and mounding plant form; overall plant shape, flattened globular; sturdy plant habit; freely basal branching habit with about six primary branches developing per plant; inflorescences held above the foliar plane on strong peduncles; bushy and dense growth habit; pinching is not required but will improve branching habit; moderately vigorous growth habit.

*Plant height, soil level to top of foliar plane*.—About 24.4 cm.

*Plant height, soil level to top of floral plane*.—About 27.1 cm.

*Plant diameter or spread*.—About 28.7 cm.

*Lateral branches*.—Length: About 10.5 cm. Diameter: About 5 mm. Internode length: About 2.9 cm. Aspect: Primary branches are mostly erect; secondary branches, about 40° from primary branch axis. Strength: Moderately strong. Texture and luster: Smooth, glabrous; glossy. Color, developing: Close to 143A. Color, developed: Close to between 143A and 146A.

Leaf & leaflet description:

*Arrangement*.—Leaves opposite and compound with three or five leaflets.

*Length, leaf*.—About 10.1 cm.

*Width, leaf*.—About 10.6 cm.

*Length, terminal leaflets*.—About 8 cm.

*Width, terminal leaflets*.—About 4.9 cm.

*Length, lateral leaflets*.—About 5.8 cm.

*Width, lateral leaflets*.—About 3.6 cm.

*Shape, leaves*.—Ovate.

*Shape, leaflets*.—Ovate.

*Apex, leaflets*.—Apiculate.

*Base, leaflets*.—Attenuate.

*Margin, leaflets*.—Coarsely serrate.

*Venation pattern, leaflets*.—Pinnate.

*Texture and luster, upper surface, leaflets*.—Smooth, sparsely pubescent; slightly velvety; slightly glossy.

*Texture and luster, lower surface, leaflets*.—Smooth, sparsely pubescent; matte.

*Color*.—Developing leaflets, upper surface: Close to 143A. Developing leaflets, lower surface: Close to 138A. Fully expanded leaflets, upper surface: Close to between NN137A and 147A; venation, close to 144A. Fully expanded leaflets, lower surface: Close to 191A; venation, close to 143A.

*Petioles*.—Length: About 2.7 cm. Width: About 4 mm. Height: About 3 mm. Strength: Moderately strong to strong. Texture and luster, upper surface: Sparsely pubescent; glossy. Texture and luster, lower surface: Smooth, glabrous; glossy. Color, upper and lower surfaces: Close to 144A.

Inflorescence description:

*Appearance and arrangement*.—Semi-double inflorescence form with ray and disc florets forming acropetally on a receptacle; inflorescences positioned above and beyond the foliar plane on strong peduncles; inflorescences face mostly upright to slightly outwardly; freely flowering habit with about nine developing and fully developed inflorescences per plant.

*Fragrance*.—None detected.

*Flowering response and flowering period*.—Early flowering habit, plants begin flowering about 61 days after planting; plants flower continuously during the autumn into the winter in The Netherlands.

*Post-production longevity*.—Inflorescences maintain good substance for about ten days on the plant; inflorescences persistent.

*Inflorescence buds*.—Height: About 1 cm. Diameter: About 1.5 cm. Shape: Flattened globular. Texture and luster: Smooth, glabrous; glossy. Color: Close to 144B to 144C; distally, tinged with close to 36A.

*Inflorescence size*.—Diameter: About 8 cm. Depth (height): About 5 cm. Disc diameter: About 1 cm; typically inconspicuous.

*Receptacles*.—Height: About 6 mm. Diameter: About 4 mm. Shape: Oblong, short. Color: Close to 145B to 145C.

*Ray florets*.—Quantity per inflorescence and arrangement: About 90 arranged in about five whorls. Length: About 3.8 cm. Width: About 1.8 cm. Shape: Broadly obovate. Apex: Obtuse to broadly acute. Base: Attenuate. Margin: Entire. Aspect: Upright to roughly horizontal and eventually downward; moderately to strongly concave. Texture and luster, upper and lower surfaces: Smooth, glabrous; velvety; matte. Color: When opening, upper surface: Close to 44B. When opening, lower surface: Close to 31C; towards the margins, close to 33B to 33C. Fully opened, upper surface: Close to 45B; venation, close to 45B; color does not change with development. Fully opened, lower surface: Close to 43B; venation, close to 26C; color does not change with development.

*Disc florets*.—Quantity per inflorescence and arrangement: About 20 massed at the center of the inflorescence in about three spiral whorls; typically inconspicuous. Length: About 1.6 cm. Diameter: About 5 mm. Shape: Tubular, elongated; apices, acute. Texture and luster, inner and outer surfaces: Smooth, glabrous; glossy. Color, when opening, inner and outer surfaces: Apex and mid-section: Close to 14A. Base: Close to between N144B and 151D. Color, fully opened, inner and outer surfaces: Apex: Close to 14A. Mid-section: Close to 14B. Base: Close to between N144B and 151D.

*Phyllaries*.—Quantity per inflorescence and arrangement: About five arranged in a single whorl. Length: About 1.3 cm. Width: About 5 mm. Shape: Elliptic. Apex: Acute. Base: Cuneate. Margin: Entire. Texture and luster, upper and lower surfaces: Smooth, glabrous; moderately glossy. Color, upper surface: Close to NN137B. Color, lower surface: Close to NN137C.

*Peduncles*.—Length, terminal peduncle: About 11.9 cm. Diameter, terminal peduncle: About 3 mm. Strength: Strong. Texture and luster: Smooth, glabrous; moderately glossy. Color: Close to 144A to 144C.

*Reproductive organs*.—Androecium, present on disc florets only: Quantity per floret: About five. Filament length: About 2 mm. Filament color: Close to 154C. Anther shape: Narrowly oblong. Anther length: About 3.5 mm. Anther color: Close to 13C. Pollen amount: Abundant. Pollen color: Close to 23A. Gynoecium, present on disc florets only: Quantity per floret: One. Pistil length: About 1.2 cm. Style length: About 5 mm. Style color: Close to 154C. Stigma diameter: About 8 mm. Stigma shape: Cleft, occasionally three-parted. Stigma color: Close to 14A and 15A. Ovary color: Close to 145D. Seeds and fruits: Seed and fruit development have not been observed on plants of the new *Dahlia* to date.

Disease & pest resistance: Plants of the new *Dahlia* have not been observed to be resistant to pathogens and pests common to *Dahlia* plants to date.

Temperature tolerance: Plants of the new *Dahlia* have been observed to tolerate high temperatures of about 35° C. and to be suitable for USDA Hardiness Zones 9 to 11.

It is claimed:

1. A new and distinct *Dahlia* plant named 'BKDAMRD' as illustrated and described.

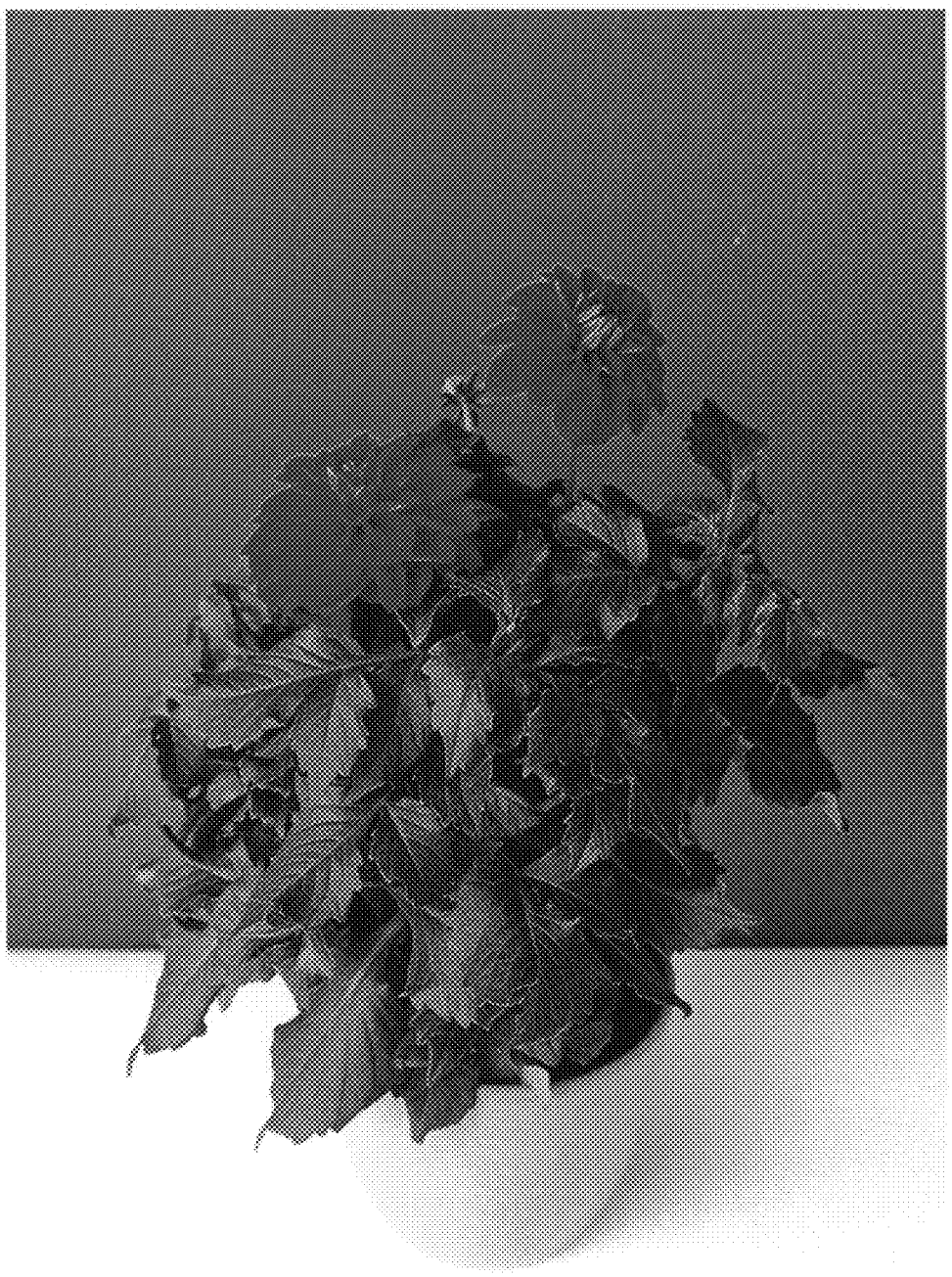

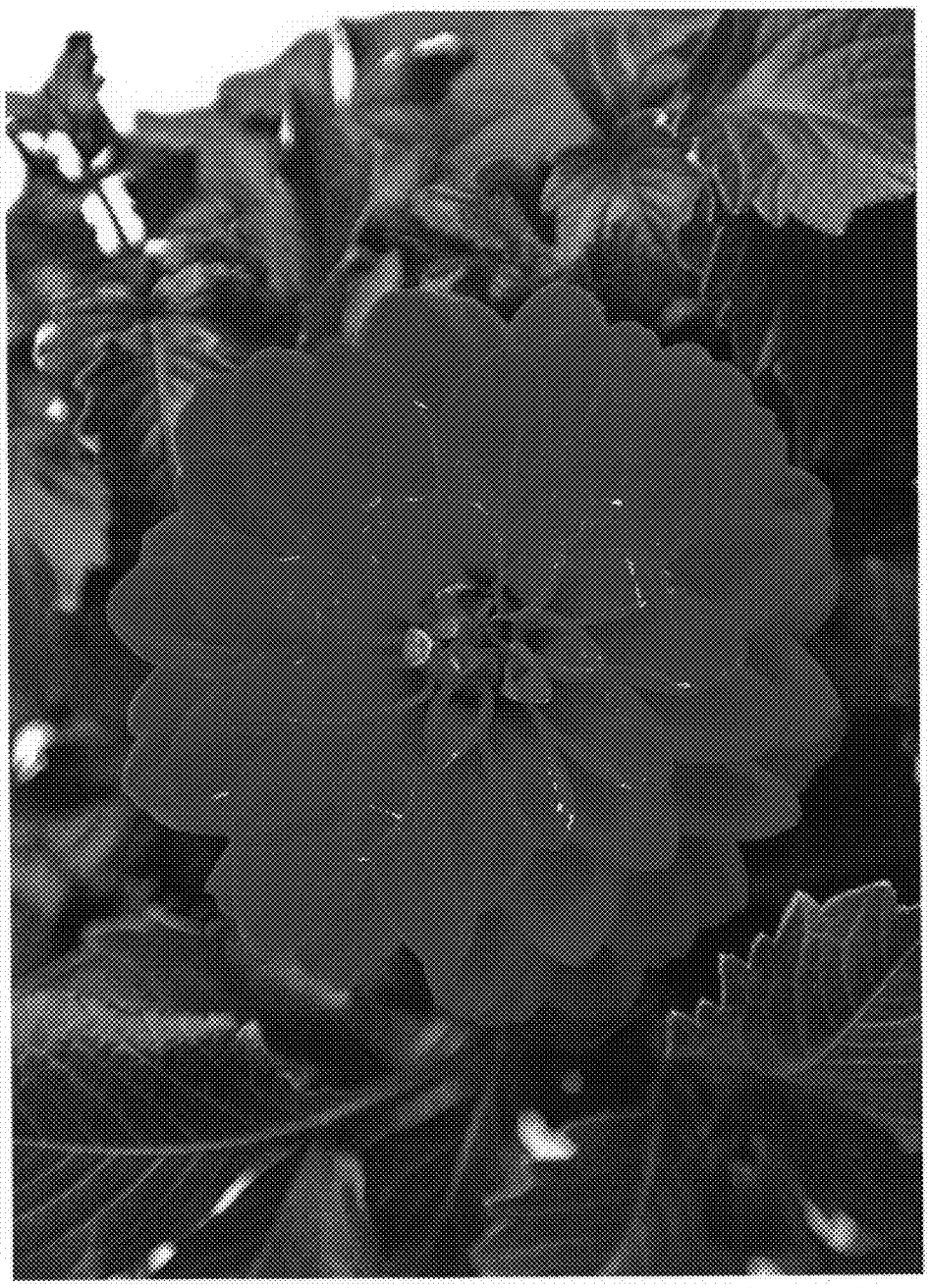

* * * * *